United States Patent [19]
Harttig et al.

[11] Patent Number: 6,159,747
[45] Date of Patent: Dec. 12, 2000

[54] ANALYTICAL TEST ELEMENT WITH A BLISTER FILLED WITH LIQUID

[75] Inventors: Herbert Harttig, Altrip; Christian Klein, Weilheim, both of Germany

[73] Assignee: Roche Diagnostics GmbH, Mannheim, Germany

[21] Appl. No.: 09/027,894

[22] Filed: Feb. 23, 1998

[30] Foreign Application Priority Data

Mar. 6, 1997 [DE] Germany .................. 197 09 090

[51] Int. Cl.[7] ................ G01N 33/543; G01N 33/558
[52] U.S. Cl. ................ 436/518; 422/56; 422/58; 422/61; 435/287.1; 435/287.2; 435/287.6; 435/287.7; 435/287.8; 435/287.9; 435/970; 435/805; 435/810; 436/169; 436/514; 436/530; 436/810
[58] Field of Search ................ 422/56, 58, 61; 435/287.1, 287.2, 287.6, 287.7, 287.8, 287.9, 970, 805, 810; 436/169, 514, 518, 530, 810

[56] References Cited

U.S. PATENT DOCUMENTS

| | | | |
|---|---|---|---|
| 4,943,522 | 7/1990 | Eisinger et al. | 436/514 |
| 4,965,047 | 10/1990 | Hammond | 422/58 |
| 5,268,306 | 12/1993 | Berger et al. | 436/527 |
| 5,595,741 | 1/1997 | Huber et al. | 530/403 |
| 5,632,993 | 5/1997 | Klein et al. | 514/23 |
| 5,646,255 | 7/1997 | Klein et al. | 530/322 |

FOREIGN PATENT DOCUMENTS

| | | |
|---|---|---|
| 0279574 | 8/1992 | European Pat. Off. . |
| 0331127 | 6/1993 | European Pat. Off. . |
| 0547029 | 6/1995 | European Pat. Off. . |
| 0571941 | 11/1997 | European Pat. Off. . |
| 9015798 | 12/1990 | WIPO . |

*Primary Examiner*—Christopher L. Chin
*Attorney, Agent, or Firm*—Fulbright & Jaworski, LLP

[57] ABSTRACT

The invention concerns an analytical test element containing an absorbent material with a sample application and detection zone and a blister filled with liquid on a support, wherein the support has a notch within the support surface such that a spike forms there when the support is bent with which the blister can be opened so that liquid escapes and comes into contact with the absorbent material as well as a process for the production of such an analytical test element and a method for determining an analyte by means of such an analytical test element.

13 Claims, 5 Drawing Sheets

Fig. 3
Fig. 4
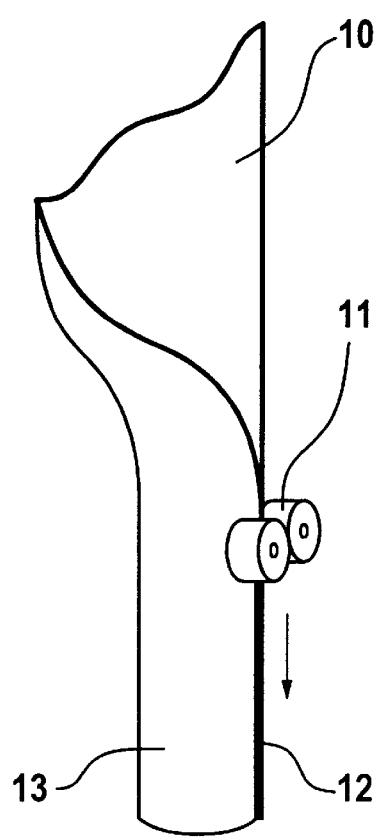
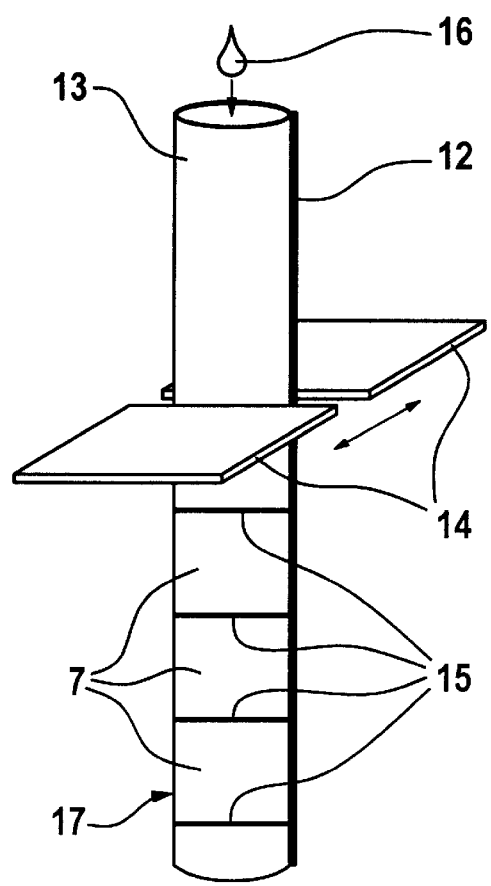

ANALYTICAL TEST ELEMENT WITH A BLISTER FILLED WITH LIQUID

BACKGROUND OF THE INVENTION

The invention concerns an analytical test element comprising an absorbent material with a sample application and detection zone and a blister filled with liquid on a support. In addition the invention concerns a process for the production of such an analytical test element and a method for determining an analyte with such an analytical test element.

So-called carrier-bound tests are often used for the qualitative or quantitative analytical determination of sample components. In these the reagents are embedded in appropriate layers of an analytical test element which is contacted with the sample. As a rule the detection reactions proceed in a liquid phase. This liquid is usually derived from the sample itself in the case of liquid samples or the liquid is applied to the sample on the analytical test element. The reaction of sample and reagents then leads to a detectable signal, in particular a colour transition which can be analysed visually or with the aid of an instrument, usually by reflection photometry. Electrochemical methods of detection are now also possible on analytical test elements.

Analytical test elements are often in the form of test strips which are essentially composed of an elongate carrier i.e. a support layer for example made of plastic material and detection layers mounted thereon as test zones. However, analytical test elements are also known that are in the form of small quadratic or rectangular plates.

Analytical test elements of the type mentioned above are for example known from the European Patent document 0 279 574. The analytical test element described in this patent contains an absorbent layer with a sample application and detection zone as well as a blister filled with liquid made of a rupturable specially shaped material within a liquid-impermeable housing. The blister is formed from a stiff but nevertheless deformable plastic in such a way that it has a dome-shaped surface in which one or several pointed, rigid infolds pointing inwards are formed. When external pressure is applied to these pointed infolds the opposite blister wall is pierced and the liquid present in the blister escapes. On contact with the absorbent layer the liquid is taken up by this layer and spreads out there by capillary force. The sample material to be examined is then reacted in the liquid with the detection reagents. The special shape of the blister is relatively complicated to manufacture. Furthermore the overall manufacture of such blisters filled with liquid can only be carried out in a discontinuous manner because firstly it must be shaped by means of injection moulding or a deep-drawing process, subsequently filled with liquid and finally sealed liquid-tight with a piercable foil.

SUMMARY OF THE INVENTION

The disadvantages of the state of the art are eliminated by the invention as characterized in more detail in the claims.

Accordingly a subject matter of the invention is an analytical test element which contains a absorbent material with a sample application and detection zone as well as a blister filled with liquid on a support wherein the support has a notch in the support surface. This notch is formed such that when the support is bent a spike is formed at this position with which the blister can be opened in such a manner that liquid escapes and comes into contact with the absorbent material.

A further subject matter of the invention is a process for manufacturing such an analytical test element. For this absorbent material and a continuous tape of liquid-filled blisters is mounted on a layer of flexible but nevertheless stiff material which has notches positioned next to one another. The individual blisters are separated in the continuous tape by transverse welding seams. The tape is applied to the layer of flexible but nevertheless stiff material in such a way that a blister located between two transverse welding seams comes to lie above a notch within the support surface. Finally individual analytical test elements are formed by cutting the flexible but nevertheless stiff layer along the transverse welding seams in the blister tape.

Finally the invention also concerns a method for the determination of an analyte by means of an analytical test element according to the invention. For this a sample is contacted with the sample application zone, the support layer is bent and the blister filled with liquid is opened with the spike that is formed. The escaping liquid contacts the sample. The analyte to be determined is then detected either in the sample application zone itself or in a detection zone into which the liquid is transported.

An important component of the analytical test element according to the invention is the support. It must on the one hand be stiff enough to support the functional elements, essentially the absorbent material with a sample application and detection zone, as well as the blister filled with liquid and stiff enough to enable the user to handle the analytical test element. On the other hand it must be possible to bend the support such that in this process a spike is formed from the notch which itself must be so stiff and solid that it can open the blister filled with liquid. Plastic materials are especially suitable for this which can be bent at the site of the notch in such a way that the necessary spike is exposed. Corresponding polyester, polystyrene or polyamide foils have proven to be particularly advantageous for this. In order to facilitate the bending of the support at the desired site, a predetermined bending point can also be provided there. This can for example comprise an appropriately thinner material cross-section or lateral notches can be incorporated which facilitate bending of the support at a predetermined position.

The notch in the support surface is preferably V-shaped so that when the support is bent along a line, a spike is formed by the upper side of the V. However, other notches are also possible provided that spiked shapes are formed when the support is bent with which the blister filled with liquid can be opened. For example W-shaped notches are also possible which form two spikes when the support is bent with which the blister can be opened.

A blister filled with liquid must be arranged above the site of the notch in the support surface such that it can be opened by the exposed spike(s) of the notch when the support is bent. For this the blister can either lie directly above the notch on the support surface and the absorbent material with the sample application and detection zone can be arranged next to it so that when the blister is opened escaping liquid is taken up by the absorbent material or the blister is located above the site of the notch of the support on absorbent material located between the blister and the support so that the spike exposed when the support is bent comes into contact with the blister through the absorbent material and opens it. In the latter case the absorbent material can have a recess at the site of the notch in the support surface or it can be arranged on the support without such a recess. If no recess is present in the absorbent material it must be designed in such a way that it can be penetrated by the exposed spike when the support is bent so that the spike can also open the blister located on the absorbent material.

Basically all materials can be used as absorbent material which are generally used in so-called dry tests for liquid uptake. Membranes have for example proven to be advantageous for this. However, fibrous, absorbent matrix materials such as fleeces, fabrics or knitted fabrics are quite especially preferred. Fleeces are very especially preferred. The fibrous matrix materials can contain glass, cellulose, polyester fibres and also viscose and polyvinyl alcohol. Fleece materials containing meltable copolyester fibres in addition to glass fibres, polyester fibres, polyamide fibres, cellulose fibres or cellulose derivative fibres as described in the European Patent Application 0 571 941 can also be used advantageously in the analytical test element according to the invention. Papers such as for example tea-bag paper can also be used well.

Basically all elements filled with liquid that can be opened with a pointed object such as that which is formed when the support of the analytical test element according to the invention is bent can be basically used as blisters. Those elements have proven to be advantageous for this which enclose liquid with a thin skin of metal, plastic or plastic-coated metal. Those blisters are particularly preferred according to the invention which are manufactured from a plastic-coated thin metal foil, preferably made of aluminium.

In order to manufacture such particularly preferred blisters the side edges of a plastic-covered metal foil are heat-welded together so that a plastic-coated metal tube is formed. Transverse thermowelding i.e. a thermal sealing at right angles to the longitudinal direction of the tube, creates a container closed at the bottom into which liquid can be filled from above through the tube opening. A renewed cross-welding above the level of the liquid or through the liquid, this process being repeated several times, produces a tape filled with liquid which contains a row of numerous blisters. If desired these blisters can be subsequently or at a later time be separated by cutting the tape along the transverse welding seams.

In order that the blister filled with liquid cannot evade the pressure of the exposed spike when the support is bent, it must either be held manually for example with a finger or by constructive measures. For this purpose the blister can for example be attached to the support along its transverse welding seams, parallel to the longitudinal direction of the test element and thus along the liquid transport within the test element after the blister is opened. Such an attachment can for example be accomplished by means of double-sided adhesive tape. This attachment is preferably achieved with hot-melt adhesive strips. In a quite especially preferred embodiment the blister is not only attached to the two longitudinal sides of the test element but also to the side of the test element opposite to that of the liquid transport direction. In this manner when the blister is opened liquid which escapes is particularly advantageously taken up by the absorbent material which is adjacent to the blister.

Another equally effective method of mounting the blister on the analytical test element comprises applying a foil which covers the blister and which stretches tight over the blister filled with liquid when the support is bent so that it cannot move out of the way. Such a foil is attached to the longitudinal sides of the support so that it does not interfere with the liquid transport in the test element. In such an embodiment it may under certain circumstances be possible to omit direct attachment of the blister on the support. Such a foil also has a mechanical protective function which prevents the blisters from being inadvertently opened by pointed objects. Furthermore such a foil, when it has an appropriate composition, can also serve as light protection for the liquid present in the blister.

Another effective method of securing the blister when the support of the test element according to the invention is bent is to mount the test element in a stable housing which covers the blister to a sufficient extent to, on the one hand, prevent it evading the spike that is formed during bending but, on the other hand, still allows the support of the test element to be bent.

The liquid located in the blister of the analytical test element according to the invention can be an elution liquid which serves to contact analyte and reagents which are located on the absorbent material of the analytical test element with sufficient liquid to enable a reaction and/or to enable transport of sample material and/or transport of reagents in the absorbent material by chromatography. The blister liquid can, however, also contain all or some of the reagents required to detect the analyte to be determined on the analytical test element according to the invention.

Accordingly the absorbent material can have different compositions. In any case the absorbent material must be arranged in relation to the blister filled with liquid in such a way that the liquid that comes out of the blister can be taken up by the absorbent material. The absorbent material of the analytical test element according to the invention contains at least one sample application and one detection zone. In the simplest case the absorbent material of the sample application and detection zone are identical. The corresponding zone is arranged in relation to the blister filled with liquid such that after the blister is opened, liquid which escapes from the blister is taken up by the absorbent material of the sample application and detection zones. If the sample application and detection zones are identical the blister liquid preferably contains at least part of the reagents necessary for the detection reaction.

However, it is also possible that the sample application and detection zones are located in different regions of the absorbent material. In this case the absorbent material can also additionally have one or several additional zones which contain reagents that are required to detect the analyte to be determined. The various zones can be contained on the same absorbent material. However, they can also be present on different absorbent materials. Basically all possible structures for analytical test elements are possible provided the sample application zone or eluant application zone are connected with the blister filled with liquid in such a manner that, when the blister is opened, liquid can pass into the sample application zone and either enable a detection of the analyte to be determined at this site when the sample application and detection zones are identical or sample material is transported from this position into the detection zone optionally via intermediate zones containing other reagents.

The analytical test element according to the invention is simple to manufacture. As already described above a blister tape filled with liquid is manufactured which is mounted on a support tape which has notches arranged next to one another within the support surface which allow a spike to be formed when the support is bent and which already contains the absorbent material in such a manner that each blister between two transverse welding seams comes to lie above a notch within the support surface. In addition it is important that the absorbent material is arranged in relation to the blister tape in such a way that when liquid escapes from the blister this is taken up by the absorbent material. Subsequently the analytical test elements according to the present invention can be separated by cutting the support tape along the transverse welding seams in the blister tape.

The described analytical test element is particularly simple to handle for analytical examinations that require liquid. According to the invention it suffices to contact the sample material to be examined with the sample application zone, to bend the support and thus open the blister filled with liquid with the spike in the support surface that is formed in this manner. Liquid that comes out of the blister contacts the sample and, depending on the structure of the analytical test element according to the invention that is described above, leads to detection of the substance to be determined in the sample application zone itself or in a separate detection zone into which the analyte to be examined is transported with the liquid. The sample to be examined can be solid or liquid. It can be applied to the analytical test element or the analytical test element can be contacted with the sample to be examined. Hence it is possible to apply liquid sample to the sample application zone of the analytical test element. It is, however, also possible to dip the analytical test element containing the sample application zone into the liquid sample to be examined until the sample application zone has been filled with liquid to be examined and is then withdrawn again from the liquid. Solid substances can also be applied to the sample application zone. However, it is also possible that for example the sample application zone is wiped over solid surfaces and in this manner solid or liquid substances reach the sample application zone which are subsequently examined.

Gaseous substances can also be examined with the analytical test element according to the invention. For this the sample application and detection zones can for example be identical. Liquid in the blister containing reagent for the detection of the gaseous analyte can be released by bending the analytical test element and is absorbed by the absorbent material. Gaseous analyte which comes into contact with the moist detection zone containing reagent will lead to a detectable signal at this site.

In all analytical methods according to the invention detectable signals which come into consideration are in particular a colour transition which can be analysed visually or with the aid of an instrument, namely by reflection photometry. In this case colour transition denotes a change in colour which is also understood to include the formation of a colour (the transition from colourless to coloured) or the disappearance of a colour (transition from coloured to colourless). The change in the intensity of a colour is also understood to be included by the term "colour transition". Furthermore a detectable signal can also be the formation or quenching of fluorescence. Electrochemical signals can also be used to determine analytes, such as current strength or potential, if the test element is equipped with appropriate electrodes in the detection zone.

BRIEF DESCRIPTION OF THE FIGURES

FIGS. 1–8 show particularly advantageous analytical test elements according to the invention, a process for the manufacture of blisters filled with liquid for such test elements and important stages of the manufacturing process for analytical test elements according to the invention.

FIGS. 3 and 4 show stages in the manufacture of a blister tape filled with liquid.

FIGS. 5–7 show important stages in the manufacture of an analytical test element according to FIG. 1 according to the invention.

FIG. 8 shows a side view of a further particularly preferred analytical test element according to the invention.

DETAILED DESCRIPTION

List of Reference Numbers
1=support
2=notch
3=spike
4=absorbent material
5=sample application zone
6=detection zone
7=blister
8=melt adhesive
9=reagent zone
10=plastic-coated metal foil
11=sealing rollers
12=longitudinal welding seam
13=plastic-coated metal tube
14=heated jaws
15=transverse welding seam
16=blister liquid
17=blister tape
18=positioning hole
19=zone carrying the blister A preferred analytical test element according to the invention is shown in FIG. 1. As can be seen from the underside of the test element as shown in FIG. 1A, a notch (2) is located in the surface of the support (1) which allows a spike (3) to be formed when the support (1) is bent. In the present case it is a V-shaped notch (2). As already set-forth above it is, however, also possible to use other forms of notches. It is only important that when the support (1) is bent a spike (3) is exposed with which the blister filled with liquid which is located on the analytical test element, can be opened. In the preferred analytical test element shown a positioning hole (18) is located in the support (1) which enables a precisely positioned assembly of the individual components of the analytical test element during its manufacturing process.

Figure 1A:
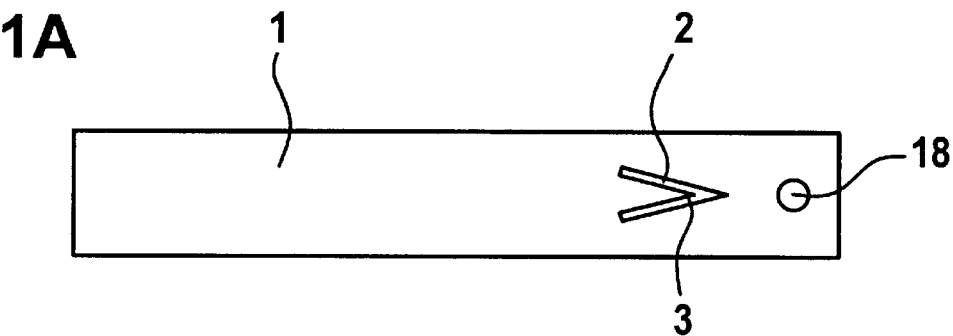
FIGS. 1A to C show a plan view from below and from above and a side view of an analytical test element according to the invention.
Figure 1B:
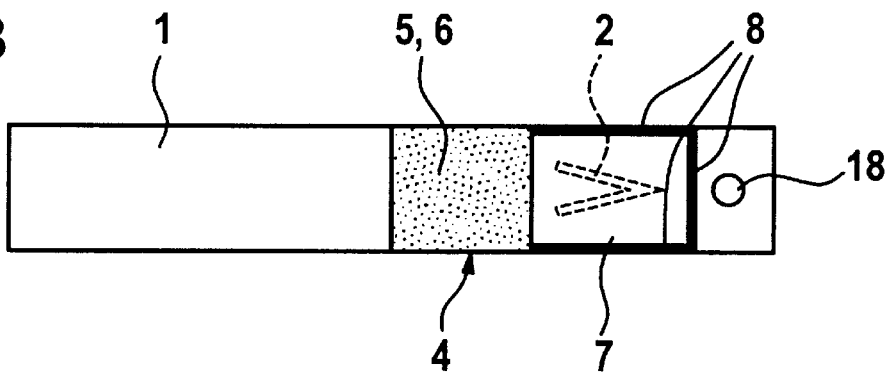

The absorbent material (4) is arranged on the upper side of the support (1) which is shown in FIG. 1B. The blister filled with liquid (7) is attached to the edge of the absorbent material (4) and of the support (1) with hot-melt adhesive strips (8) in such a way that it is located above the notch (2) of the support (1). The absorbent material is larger than the base area of the blister (7) so that an area of the absorbent material (4) lies exposed next to the blister (7) which is not covered by the blister (7). This area of the absorbent material (4) contains the sample application zone (5) and the detection zone (6) of the analytical test element according to the invention. In the case of the preferred analytical test element which is shown in FIG. 1 the sample application zone (5) and detection zone (6) are identical i.e. the sample to be examined is applied to the region of the absorbent material (4) in which the analyte to be determined is detected. The blister (7) must not be attached in such a way that when liquid escapes it prevents or interferes with the uptake of liquid into the absorbent material (4) or transport of the liquid into the sample application zone (5) and detection zone (6). In the present example the blister (7) is attached on three sides with hot-melt adhesive strips (8) so that when the support (1) is bent the blister (7) cannot evade the exposed spike (3) of the notch (2).

Figure 1C:
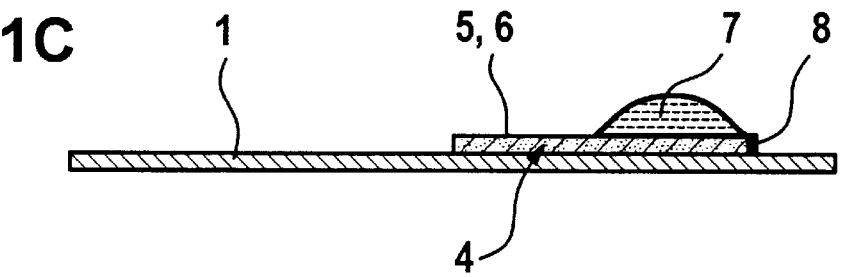
Figure 1D:
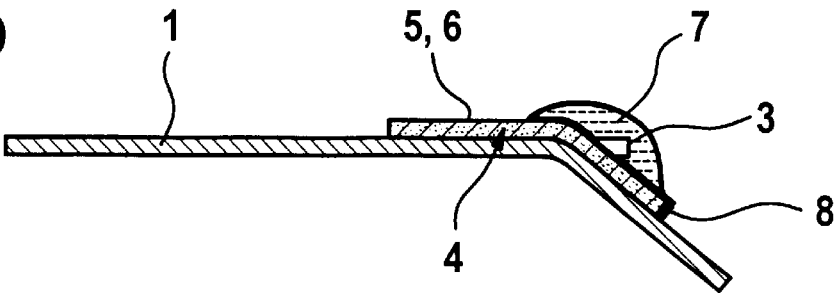
FIG. 1D shows the side view of an analytical test element according to the invention in a bent state.

In order to carry out an analyte determination the sample material to be examined is applied to the sample application zone (5) of the absorbent material (4) on the preferred analytical test element shown in cross-section in FIG. 1C. When the support (1) is bent as shown in the cross-section in FIG. 1D the spike (3) penetrates into the blister filled with liquid (7) and liquid escapes from the blister (7). The liquid is taken up by the absorbent material (4) and spreads there in the direction of the sample application zone (5). A detection reaction then takes place in the liquid medium which is then present at this site which leads to a signal which can be observed in the detection zone (6) that is identical to the sample application zone (5). In a preferred embodiment it is a colour signal which can either be observed from above or from below through the support (1), if the support (1) is made in an appropriate manner. For an observation through the support (1), the support (1) must either be transparent or have an opening in the area of the detection zone (6) through which the absorbent material (4) can be observed in the area of the detection zone (6). The reagents required for the detection reaction can either be completely present in or on the absorbent material (4) or they can be contained in the liquid of the blister (7). It is of course also possible that parts of the detection reagent are located in the liquid of the blister (7) and other parts are located in or on the absorbent material (4). A division of the detection reagent is above all necessary when the reagent components are such that they would undergo an interfering interaction on direct contact with one another.

Figure 2A:
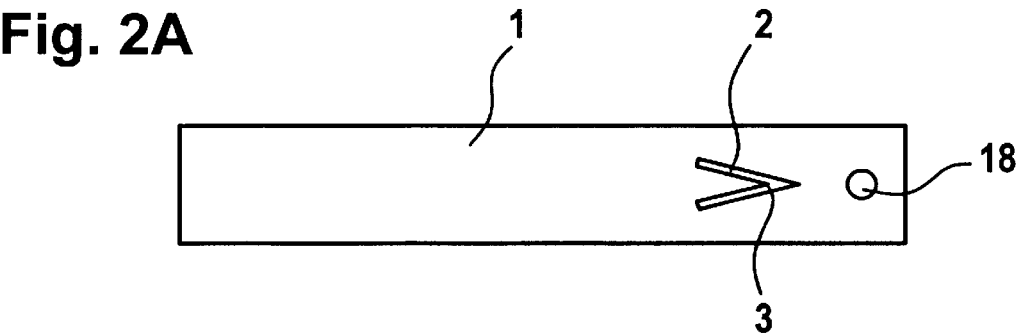
FIGS. 2A to C show a plan view from below and from above and a side view of a further particularly preferred analytical test element according to the invention.
Figure 2B:
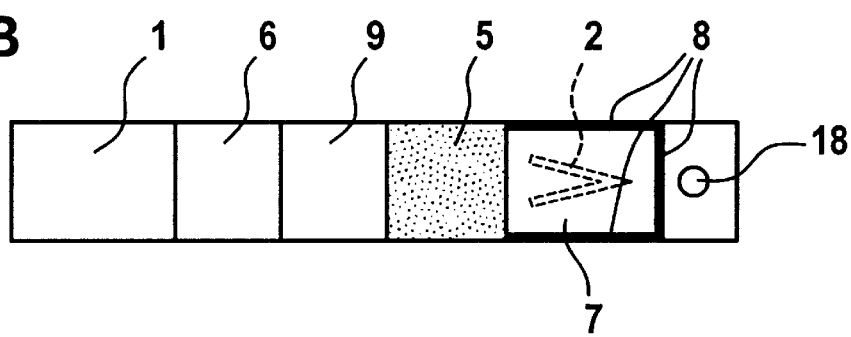
Figure 2C:
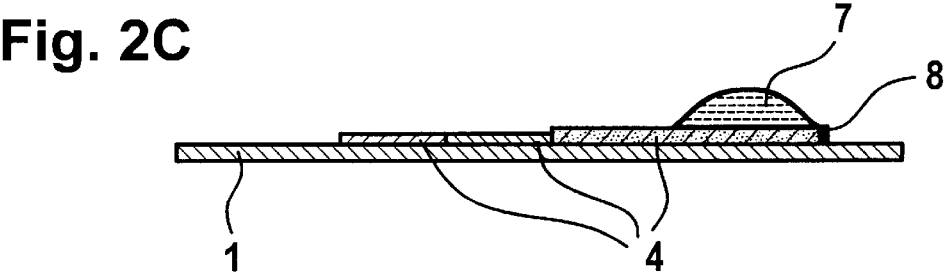

Another preferred embodiment of the analytical test element is shown in FIG. 2. In this case the absorbent material (4) is divided into different functional regions located next to one another. The blister (7) is directly adjacent to the sample application zone (5) which is adjoined by a reagent zone (9) in which the reagents required for the detection reaction are located. The analyte is determined in the detection zone (6) which is arranged next to the reagent zone (9) in such a way that the reagent zone (9) is located between the sample application zone (5) and detection zone (6). Such an analytical test element according to the invention can be used to particular advantage when it is necessary to wait for some time before starting and carrying out the detection reaction after the sample is applied. If sample stabilizing substances are present in the sample application zone the sample can be stored there for a relatively long period after it is applied to the sample application zone before the detection reaction is started and carried out by bending the support (1) and opening the blister (7) filled with liquid.

Blisters whose manufacture is illustrated in FIGS. 3 and 4 which show characteristic intermediate products have proven to be particularly advantageous for use in the analytical test elements according to the invention. The manufacturing process is simple to carry out and comprises the welding shown in FIG. 3 of for example a plastic-coated metal foil (10), for example a plastic-coated aluminium foil, at the longitudinal edges of the foil to form a plastic-coated metal tube (13). In this manner it is possible to form a metal tube (13) from a continuous sealable aluminium tape passed through a pair of heated rollers as shown in FIG. 3 as sealing rollers (11). FIG. 4 shows how this metal tube (13) can be sealed at right angles to the feed direction by a pair of heated jaws (14) in a synchronized process. If the tube is guided from top to bottom it is then possible to feed in liquid (16) above the transverse welding seam (15) and thus manufacture blisters (7) filled with liquid by a synchronized cross-welding which are firstly formed as a blister tape (17) and then can later be separated. Whereas it is possible to fill the liquid (16) into the metal tube (13) in a cycle with a time delay to the closing cycle of the heated jaws (14) so that a certain amount of liquid is filled into a piece of the tube that is closed at the bottom and subsequently a transverse welding seam (15) is formed above the level of liquid with the aid of the heated jaws (14), it is also possible to fill in a larger amount of liquid (16) into the metal tube (13) closed at the bottom after a first sealing of the metal tube (13) by a transverse welding seam (15) and then to form transverse welding seams (15) with the heated jaws (14) through the liquid (16). The advantage of the latter process is that almost no air is enclosed in the blisters (7).

Figure 5:
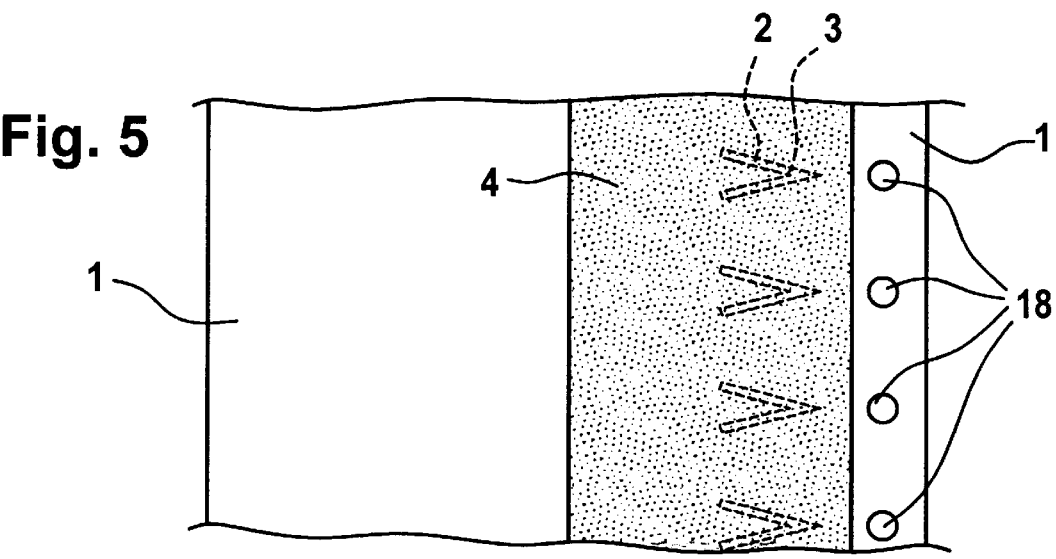
Figure 6:
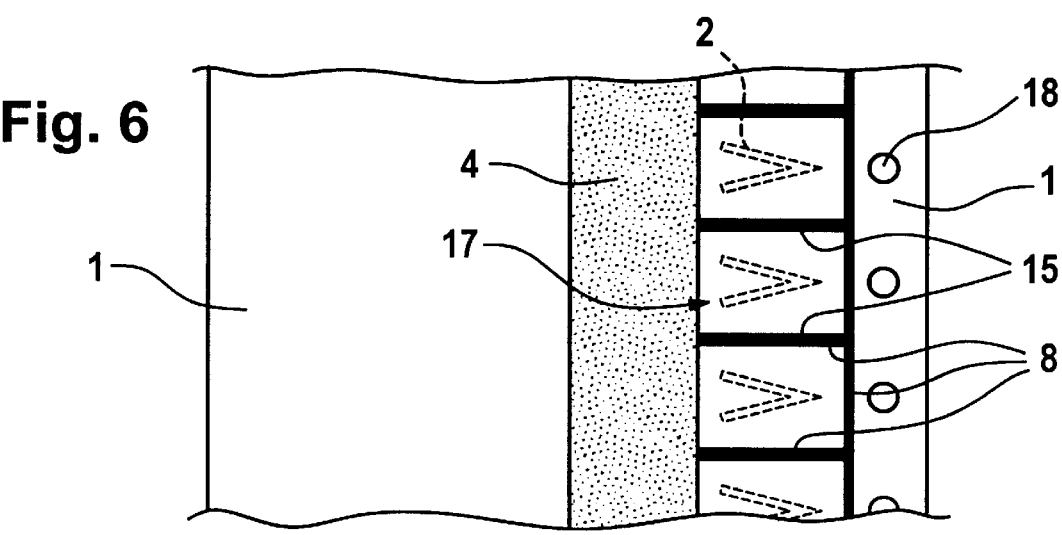
Figure 7:
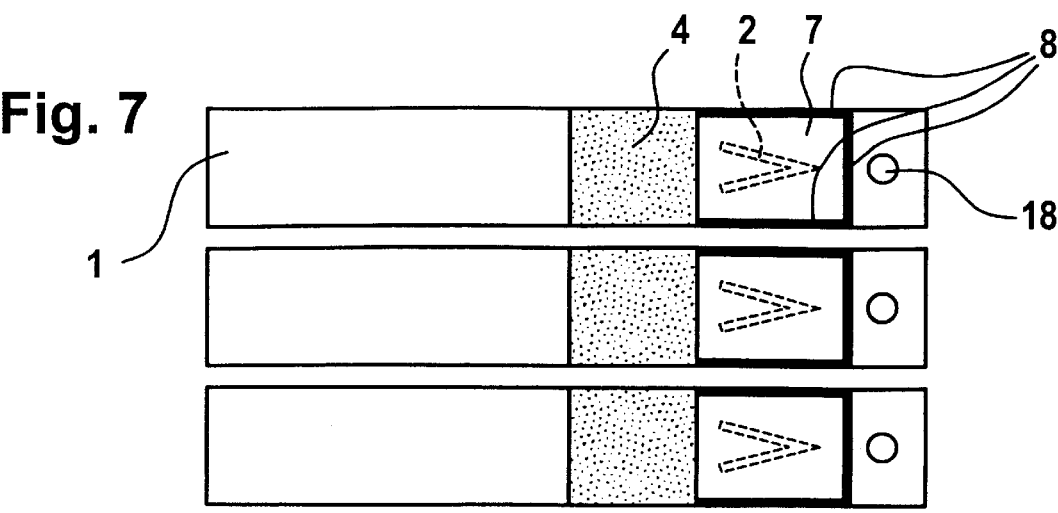

Important process steps are shown in FIGS. 5 to 7 for a preferred manufacturing process of preferred analytical test elements according to the invention as shown in FIG. 1. For the manufacture of such preferred analytical test elements according to the invention, a support (1) in the form of a long tape is used and provided with adjacent notches (2) which allow a spike to be formed when the support (1) is bent. The absorbent material (4) also in the form of a long tape is mounted on the support (1) over these notches (2). This process stage is shown in FIG. 5.

A blister tape (17) is attached to the absorbent material (4) with hot-melt adhesive (8) in such a way that the blisters (7) filled with liquid are located above the notches (2). The transverse welding seams (15) are each located between the two notches (2). Such an arrangement is made possible by the positioning holes (18) which are located at the edge of the support (1) which is present as a tape. This process stage is shown in FIG. 6.

After all process steps are completed, the tape is cut along the transverse welding seams (15) of the blister tape (17) and in this manner the individual analytical test elements according to the invention are prepared. In order that no liquid escapes from the blisters (7) during this separation of the analytical test elements according to the invention, it is of course necessary that the transverse welding seams (15) have an appropriate width and also that the cutting process can be carried out reproducibly and exactly so that the transverse welding seam is cut in such a manner that the sides of the blisters are not opened.

The separated analytical test elements are shown in FIG. 7.

These test elements are not only simple and thus cheap to manufacture but, due to their construction, are simply to handle for such analytical examinations which require liquid.

The invention is elucidated further by the following examples.

DETAILED DESCRIPTION OF PREFERRED EMBODIMENTS

Example 1: Manufacture of a Blister Tape (17)

A 26 mm wide, 30 $\mu$m thick aluminium foil that is furnished with adhesion agent and a polyethylene coating of 15 g/m$^2$ (manufacturer: Alu-Singen Company, Singen, Germany) is heat-sealed in a continuous process to form a tube. The width of the seam is 2.5 mm, the roller temperature is 180° C., the speed is 0.2 m/min.

A transverse welding device is located below the welding station. The transverse welding station operates with two heated jaws which have a temperature of 180° C. and a welding time of 4 seconds. The tube formed in the longitudinal welding station is filled to a height of ca. 10 cm with distilled water. Cross-welding is carried out at an average distance of 12 mm. The width of the seams is 4 mm.

Example 2: Manufacture of the Support (1) in the Form of a Tape

A 360 μm thick polyester foil (type Melinex, manufacturer ICI Company, Dumflies, UK) serves as the support (1). The support foil is covered with hot-melt adhesive spots of ca. 0.8 mm diameter (type Dynapol, manufacturer Dynamit Nobel, Troisdorf, Germany) over a width of 40 mm. A pilot hole as well as V-shaped notch is introduced at a distance of 12 mm on a roller stamping device. The foil is cut to a width of 72 mm on a roller cutting machine.

Example 3: Manufacture of Analytical Test Elements According to the Invention

The support (1) from example 2, a 40 mm wide paper (type VLS 353, manufacturer: Boehringer Mannheim GmbH Company, Mannheim, Germany) and the blister tape (17) of example 1 are thermally bonded in a timed manner at right angles to the longitudinal direction. The sealing distances and positions are regulated by the pilot holes. The band that forms is reeled up and cut in a later step into strips of 12 mm width on a hole-controlled cutting machine.

Example 4: Simple Function Test

Very small amounts of Congo red in crystalline form are applied to a smooth surface. The surface is wiped with the paper end of test element manufactured according to example 3. Almost no colouration of the paper can be seen with the naked eye.

The support (1) of the test element is subsequently bent in the area of the V-shaped cut and is bent straight again. The blister (7) is perforated on bending, the water escapes from the blister (7) and is transported along the paper by capillary forces. A very clearly visible red colour forms in the area which had been wiped over the surface contaminated Congo red.

These examples show that it is possible to achieve an extremely simple test design. The principle can also be used for more complicated tests. Hence by incorporating systems capable of reaction into the liquid in the blister (7) as well as by impregnations in the paper it is possible to accomplish diverse detection reactions.

Example 5: Determination of Cocaine

A. Production of the Immunological Reagents a. Production of Benzoylecgoninemaleimidoethylamide 1 g N-hydroxysuccinimide and 1.8 g dicyclohexyl-carbodiimide are added to 2.4 g benzoylecgonine hydrochloride in 200 ml dry acetonitrile and stirred for 3 hours. The precipitate is removed by filtration, the filtrate is concentrated by evaporation, taken up in nitromethane and again filtered. After removing the solvent by evaporation, it is triturated with ether. 1.13 g benzoylecgonine succinimidyl ester is obtained. This product is taken up in 100 ml dry acetonitrile together with 0.47 g maleinimidoethylamine hydrochloride (see WO 90/15798). 1.1 g triethylamine is added and it is stirred for 12 hours at room temperature. The reaction mixture is concentrated by evaporation, taken up in 50 ml ethyl acetate and shaken out three times with sodium hydrogen carbonate solution. The ethyl acetate phase is concentrated by evaporation and the product is converted into the hydrochloride by taking it up in 10 ml dioxane saturated with HCl. It is filtered, washed with ether and in this manner 1 g benzoylecgonine maleimidoethylamine hydrochloride is obtained.

b. Production of the Cocaine Immunogen 300 mg bovine serum albumin in 25 ml 0.1 mol potassium phosphate buffer pH 8.5 is reacted for 3 hours at room temperature with 106.6 mg S-acetylthiopropionic acid succinimidyl ester dissolved in 5 ml dioxane. The modified bovine serum albumin is separated from low molecular reaction products by gel chromatography over ACA 202 with 0.1 mol potassium phosphate buffer pH 8.5. A solution of 310.5 mg product in 57.5 ml potassium phosphate buffer pH 8.5 is obtained.

An amount of solution that corresponds to 100 mg of the modified bovine serum albumin is reacted with 4.7 ml 1 molar hydroxylamine solution. Afterwards 49.4 mg benzoylecgoninemaleimidoethylamide hydrochloride is added and it is allowed to react for 12 hours at 4° C. The cocaine immunogen obtained is separated from low molecular reaction products by gel chromatography over ACA 202 with 0.1 mol potassium phosphate buffer pH 8.5. 95 mg cocaine immunogen dissolved in 0.1 molar potassium phosphate buffer pH 8.5 is obtained.

c. Isolation of Antibodies to Cocaine 10 sheep were immunized with the cocaine immunogen in complete Freund's adjuvant. In each case the dose was 200 μg immunogen per animal for the first and each subsequent immunization. The immunizations were carried out at monthly intervals. The sera obtained were examined in a microtitre plate assay for the presence of antibodies to cocaine. For this streptavidin-coated microtitre plates were incubated with benzoylecgonine-[N'-biotinylaminocaproyl-(3,6-dioxa-8-aminooctyl)amide], prepared from benzoylecgonine succinimidyl ester and N-(biotinylaminocaproyl)-1,8-diamino-3,6-dioxaoctane and washed, subsequently incubated with the sera to be examined, washed again and incubated with a conjugate of peroxidase and a rabbit anti-sheep immunoglobulin for the detection, washed and substrate was added. The relative affinities for cocaine were determined similarly to example 12 from EPA 0 547 029. Sera from S 4987 with a good affinity for cocaine were selected for further investigations.

d. Preparation of Conjugates of Antibodies to Cocaine and Alkaline Phosphatase

Polyclonal antibody to cocaine from sheep that has been DE purified (PAB<cocaine>S-IGG(DE)) is isolated by means of ammonium sulphate precipitation and DEAE-Sepharose chromatography from delipidated crude serum (sheep) according to processes known to a person skilled in the art.

Immunosorptive Purification of PAB<BZE<S-IGG(DE)

Preparation of a Cocaine Immunoadsorber

The cocaine polyhapten from example 5e (without the biotinylation step) is bound to a glutardialdehyde-activated affinity adsorbent (activated Spherosil; Boelrringer Mannheim, order No. 665 525) according to the manufacturer's instructions.

Immunosorption (PAB<cocaine>S-IGG(DE)) is dialysed against PBS/azide (50 mmol/l potassium phosphate, pH 7.5, 150 mmol/l NaCl, 0.1% Na azide) and subsequently applied within 2 hours at room temperature to a suitably dimensioned adsorbent column (depending on the binding capacity of the adsorber and the titre of the IGG(DE)). After washing out the non-bound protein with PBS/azide, the bound antibody is eluted with 1 M propionic acid at room temperature. The eluate is dialysed against 30 mM sodium phosphate buffer pH 7.1.

Preparation of PAB<BZE<S-IGG(IS)-AP Conjugates

Activation of the IGG

The immunosorptively purified IGG is incubated for 1 hour at 25° C. at a concentration of 10 mg protein/mi in 30 mM sodium phosphate buffer pH 7.1 with a 5-fold excess of maleimido-hexanoyl-N-hydroxysuccinimide ester (MHS). The reaction mixture is stopped by adding a 100-fold molar excess of L-lysine/HCl in relation to MHS and dialysed against 10 mM potassium phosphate, 50 mM NaCl, 10 mM MgCl$_2$, pH 6.1.

Activation of Alkaline Phosphatase (AP)

The alkaline phosphatase (EIA quality, Boehringer Mannheim, order no. 567 744) is incubated for 1 hour at 25° C. at a concentration of 10 mg protein/ml in 30 mM triethanolamine, 3 M NaCl, 0.1 mM ZnCl$_2$, 1 mM MgCl$_2$, pH 7.0 with a 30-fold molar excess of succinimidyl-acetylthiopropionate (SATP). The reaction mixture is stopped by adding L-lysine/HCl to a final concentration of 10 mM and dialysed against 10 mM potassium phosphate, 50 mM NaCl, pH 7.5. In order to deacetylate the protected SH group, 1 M hydroxylamine solution pH 7.5 is added to a final concentration of 20 mM and 0.1 M EDTA solution to a final concentration of 0.5 mM and incubated for 15 min at 25° C. The activated AP solution is used immediately for the coupling.

Coupling

The solutions of activated AP and of the activated IGG are mixed in equimolar amounts, the pH is adjusted to 6.8–7.0 and the AP concentration is adjusted to 5 mg/ml with redistilled water. After 3 hours reaction at 25° C. the reaction mixture is stopped by the sequential addition of N-ethylmaleimide (ad 5 mM, 30 min, 25° C.) and 1 M hydroxylamnine solution pH 7.5 (ad 20 mM, 1 hour, 25° C.). The conjugate solution is dialysed against 50 mM triethanolamine/HCl, 150 mM NaCl, 1 mM MgCl$_2$, 0.1 mM ZnCl$_2$, pH 7.6 and supplemented to a final concentration of 10 mg/ml bovine serum albumin and 3 M NaCl.

e. Preparation of a Biotinylated Cocaine Polyhapten

Rabbit IgG at a concentration of 25 mg/ml in phosphate buffer pH 8 is reacted with a 6-fold molar amount of S-acetylthiopropionic acid succinimidyl ester dissolved in dimethylsulfoxide. After 1 hour at 25° C. the reaction is stopped by addition of a solution of 1 mol/l lysine. This is followed by dialysis against 0.1 mol/l potassium phosphate buffer, pH 6 containing 1 mmol/l EDTA. Subsequently the pH is adjusted to 7.8, 1 mol/l hydroxylamine solution, pH 7.5 is added to a final concentration of 20 mmol/l and it is incubated for 1 hour at 25° C. For the coupling a 5-fold molar excess of benzoylecgoninemaleimidoethylamide hydrochloride is dissolved in dimethylsulfoxide and added while stirring to the solution of the rabbit IgG modified with sulfhydryl groups. After incubation at 25° C. for 2 hours, the reaction is stopped by the successive addition of 0.1 mol/l cysteine solution to a final concentration of 1 mmol/l and 0.5 mol/l iodoacetamide solution to a final concentration of 5 mmol/l. The mixture is dialysed overnight against 0.1 mol/l potassium phosphate buffer, pH 8.5 and concentrated by membrane filtration to a protein concentration of 10 mg/ml. Afterwards the cocaine polyhapten obtained is biotinylated with an 8-fold molar excess of biotinylcaproic acid succinimidyl ester dissolved in dimethylsulfoxide. The preparation is dialysed against 20 mmol/l sodium acetate, pH 4.3 and purified by means of FPLC.

B. Construction of an Analytical Test Element According to FIG. 8

Zone Carrying the Blister (19)

Polyester fleece from the Binzer Company, Hatzfeld, Federal Republic of Germany. This is a pure polyester fleece which is stiffened with 10% Kuralon®. The thickness is 1.0–1.2 mm, the absorptive capacity is 1800 ml/m$^2$.

Sample Application Zone (5)

A mixed fleece of 80 parts polyester and 20 parts cell-wool stiffened with 20 parts Kuralon® at a thickness of 0.32 mm with an absorptive capacity of 500 ml/m$^2$ is impregnated with the following solution and subsequently dried: 3.8 10$^{-8}$ mol/l of the conjugate prepared according to A.d. of anti-cocaine antibody and alkaline phosphatase, 3 mmol/l NaCl, 1 mmol/l MgCl$_2$, 0.1 mmol/l ZnCl$_2$, 30 mmol/l triethylamine pH 7.6.

Reagent Zone (9) as a Capture Matrix

A fleece of 100% linters stiffened with 2% Etadurin having a thickness of 0.35 mm and an absorptive capacity of 372 ml/m$^2$ is impregnated with the following solution and subsequently dried: 10 mmol/l sodium phosphate pH 7.5, 200 mg/l polymerized streptavidin (preparation according to example 1 d in EP-B-0 331 127).

The pre-impregnated fleece is subsequently again impregnated with 10 mmol/l sodium phosphate pH 7.5, 200 mg/l biotinylated cocaine polyhapten from example Ae and subsequently dried.

Detection Zone (6)

A fleece of 100% linters stiffened with 2% Etadurin at a thickness of 0.35 mm and an absorptive capacity of 372 ml/m$^2$ is used.

The absorbent matrices are bonded with a slight overlap onto a polyester foil (type Melinex, ICI, Dumfries, UK) according to example 2 so that the zone 19 comes to lie above a V-shaped notch in the polyester foil. A blister tape filled with buffer solution (150 mmol/l NaCl, 50 mmol/l potassium phosphate buffer pH 7.2) which is prepared analogously to example 1 is attached with hot-melt adhesive to the material of the zone 19 analogously to example 3 and subsequently strips of 12 mm width are cut which form the analytical test elements according to FIG. 8.

C. Measurement

Figure 8:
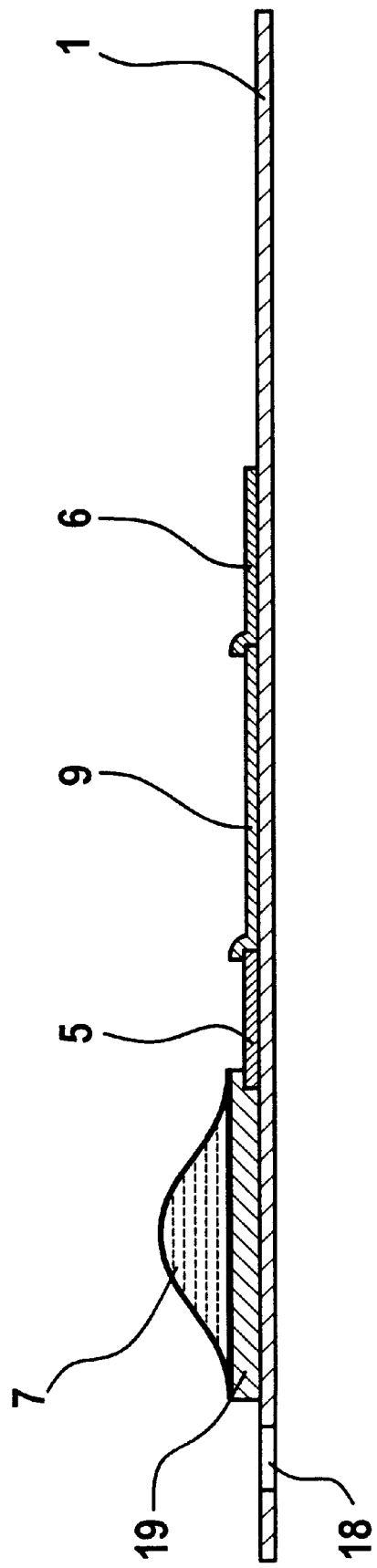

Cocaine is applied to the sample application zone (5) of the analytical test element according to FIG. 8. Afterwards the support (1) of the test element is bent in the area of the V-shaped notch and is again bent straight. On bending the blister (7) is perforated, the buffer solution escapes and is taken up by the zone carrying the blister (19).

The liquid chromatographs into the detection zone (6). A round part is punched out of this with a DIN 821 punch and placed with the fleece upper side in a microtitre plate well. 100 μl substrate solution (Lumiphos 530, preparation of di-sodium 3-(methoxyspiro{1,2-dioxetan-3,2'-tricyclo[3.3.1.1.$^{3,7}$]decane}phenyl phosphate, Boehringer Mannheim) is added in a luminescence microtitre plate reader (Luminoscan). The luminescence is measured over a period of 10 min.

In order to determine the blank value an analytical element is used to which no cocaine has been added.

| applied amount of cocaine (pg) | luminescence [rel. units/60 sec.] |
| --- | --- |
| blank value | 60.46 |
| 1 | 76.86 |
| 10 | 106 |
| 100 | 134.4 |
| 1000 | 244.7 |

What is claimed is:

1. An analytical test element comprising absorbent material with a sample application zone and detection zone, both zones being arranged on the same absorbent material or on different absorbent materials, and a blister filled with liquid on a support, wherein the support has a notch within the support surface such that a spike forms there when the support is bent which enables the blister to be opened so that liquid escapes and contacts with the absorbent material.

2. The analytical test element as claimed in claim 1, wherein the blister is in contact with the absorbent material.

3. The analytical test element of claim 1, wherein said sample application and said detection zone are identical with regard to the absorbent material.

4. The analytical test element of claim 1, wherein said sample application zone and said detection zone are separate regions.

5. The analytical test element of claim 1, wherein said sample application zone and said detection zone are composed of different materials.

6. The analytical test element of claim 1, wherein said notch within the support surface is V-shaped.

7. The analytical test element of claim 1, wherein said blister is mounted on said absorbent material.

8. The analytical test element of claim 1, wherein said blister is directly attached to said support.

9. The analytical test element of claim 1, wherein said blister is held on said support by means of a foil which stretches over said blister and is directly attached to said support in front of and behind said blister.

10. The analytical test element of claim 1, wherein the analytical element is located in a housing in such a way that said support can be bent so that a spike forms with which said blister can be opened and that said blister is covered by said housing to such an extent that said blister cannot avoid said spike when said support is bent.

11. The analytical test element of claim 1, wherein the absorbent material outside of said sample application zone and said detection zone is covered in such a way by a liquid-impermeable foil that it is located between said foil and said support.

12. The analytical test element of the claim 2, wherein said sample application and said detection zone are identical with regard to the absorbent material.

13. The analytical test element of the claim 2, wherein said sample application zone and said detection zone are separate regions.

* * * * *